US012138328B2

(12) United States Patent
Lynch et al.

(10) Patent No.: US 12,138,328 B2
(45) Date of Patent: *Nov. 12, 2024

(54) RHEOLOGICAL SOLID COMPOSITION

(71) Applicant: The Procter & Gamble Company, Cincinnati, OH (US)

(72) Inventors: Matthew Lawrence Lynch, Mariemont, OH (US); Brandon Philip Illie, Felicity, OH (US); Taotao Zhu, West Chester, OH (US); Jamie Lynn Dria, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/225,147

(22) Filed: Apr. 8, 2021

(65) Prior Publication Data

US 2021/0315783 A1 Oct. 14, 2021

Related U.S. Application Data

(60) Provisional application No. 63/007,965, filed on Apr. 10, 2020.

(51) Int. Cl.
*A61K 8/02* (2006.01)
*A61K 8/36* (2006.01)
*A61Q 15/00* (2006.01)

(52) U.S. Cl.
CPC ............ *A61K 8/0245* (2013.01); *A61K 8/361* (2013.01); *A61Q 15/00* (2013.01); *A61K 2800/20* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 823,725 | A | 6/1906 | Hayden |
| 3,293,684 | A | 12/1966 | Otto |
| 3,956,158 | A | 5/1976 | Donaldson |
| 4,107,289 | A | 8/1978 | Kaufman |
| 4,203,857 | A | 5/1980 | Dugan |
| 4,322,400 | A | 3/1982 | Yuhas |
| 4,486,404 | A | 12/1984 | Weinert |
| 4,806,340 | A | 2/1989 | Gaffar |
| 4,808,467 | A | 2/1989 | Suskind et al. |
| 5,144,729 | A | 9/1992 | Austin et al. |
| 5,160,739 | A | 11/1992 | Kanga |
| 5,340,492 | A | 8/1994 | Kacher et al. |
| 5,340,571 | A | 8/1994 | Grace |

(Continued)

FOREIGN PATENT DOCUMENTS

| | | |
|---|---|---|
| CA | 680113 A | 2/1964 |
| CN | 107440935 A | 12/2017 |

(Continued)

OTHER PUBLICATIONS

PCT Search Report and Written Opinion for PCT/US2021/026298 dated Jul. 26, 2021.

(Continued)

*Primary Examiner* — Kyung S Chang
(74) *Attorney, Agent, or Firm* — Kathleen Y. Carter

(57) ABSTRACT

A rheological solid composition comprising a crystallizing agent and an aqueous phase.

16 Claims, 3 Drawing Sheets

(56) References Cited

U.S. PATENT DOCUMENTS

| | | |
|---|---|---|
| 5,425,892 A | 6/1995 | Taneri et al. |
| 5,436,278 A | 7/1995 | Imashiro et al. |
| 5,525,397 A | 6/1996 | Shizuno et al. |
| 5,585,092 A | 12/1996 | Trandai et al. |
| 5,605,681 A | 2/1997 | Trandai et al. |
| 5,691,035 A | 11/1997 | Chappell et al. |
| 5,846,520 A | 12/1998 | Guskey et al. |
| 5,916,590 A | 6/1999 | Cody et al. |
| 6,042,815 A | 3/2000 | Kellner et al. |
| 6,143,393 A | 11/2000 | Abe et al. |
| 6,241,835 B1 | 6/2001 | Abe et al. |
| 6,245,413 B1 | 6/2001 | Kenmochi et al. |
| 6,329,308 B1 | 12/2001 | Kenmochi et al. |
| 6,550,092 B1 | 4/2003 | Brown et al. |
| 6,554,937 B1 | 4/2003 | Kenmochi et al. |
| 6,774,070 B1 | 8/2004 | Kenmochi et al. |
| 6,777,064 B1 | 8/2004 | Brown et al. |
| 6,797,357 B2 | 9/2004 | Fereshtehkhou et al. |
| 6,813,801 B2 | 11/2004 | Tanaka et al. |
| 6,936,330 B2 | 8/2005 | Fereshtehkhou et al. |
| 7,003,856 B2 | 2/2006 | Hayashi et al. |
| 7,041,277 B2 | 5/2006 | Holme |
| 7,291,359 B2 | 11/2007 | Haskett et al. |
| 7,386,907 B2 | 6/2008 | Otsuka et al. |
| 7,560,398 B2 | 7/2009 | Zillig et al. |
| 7,566,671 B2 | 7/2009 | Hoadley et al. |
| 7,712,178 B2 | 5/2010 | Yamada |
| 7,779,502 B2 | 8/2010 | Fujiwara et al. |
| 7,937,797 B2 | 5/2011 | Tsuchiya et al. |
| 8,075,977 B2 | 12/2011 | Curro et al. |
| 8,093,192 B2 | 1/2012 | Liu et al. |
| 8,146,197 B2 | 4/2012 | Yamada |
| 8,151,402 B2 | 4/2012 | Takabayashi et al. |
| 8,161,594 B2 | 4/2012 | Policicchio et al. |
| 8,186,001 B2 | 5/2012 | Tsuchiya et al. |
| 8,225,453 B2 | 7/2012 | Yamada |
| 8,245,349 B2 | 8/2012 | Tsuchiya et al. |
| 8,435,625 B2 | 5/2013 | Ruehe et al. |
| 8,528,151 B2 | 9/2013 | Przepasniak |
| 8,536,074 B2 | 9/2013 | Fereshtehkhou et al. |
| 8,617,685 B2 | 12/2013 | Yamada |
| 8,646,144 B2 | 2/2014 | Wada et al. |
| 8,752,232 B2 | 6/2014 | Otsuka et al. |
| 8,756,746 B2 | 6/2014 | Policicchio |
| 8,763,197 B2 | 7/2014 | Policicchio et al. |
| 8,793,832 B2 | 8/2014 | Yamada |
| 8,851,776 B2 | 10/2014 | Schwarz et al. |
| 8,858,971 B2 | 10/2014 | Rao |
| 9,113,768 B2 | 8/2015 | Wada et al. |
| 9,198,553 B2 | 12/2015 | Policicchio |
| 9,204,775 B2 | 12/2015 | Pung et al. |
| 9,296,176 B2 | 3/2016 | Escaffre et al. |
| 9,339,165 B2 | 5/2016 | Vetter et al. |
| 9,622,943 B2 | 4/2017 | Scala et al. |
| 10,076,583 B2 | 9/2018 | Lynch |
| 10,143,764 B2 | 12/2018 | Lynch |
| 10,821,056 B2 | 11/2020 | Swartz et al. |
| 10,835,455 B2 | 11/2020 | Payne et al. |
| 10,932,996 B2 | 3/2021 | Baig et al. |
| 11,812,909 B2 | 11/2023 | Lynch |
| 2001/0048933 A1 | 12/2001 | L Alloret |
| 2002/0160088 A1* | 10/2002 | Sakaguchi ............. B01D 15/00 210/671 |
| 2003/0021760 A1 | 1/2003 | Kumar et al. |
| 2003/0053980 A1 | 3/2003 | Dodd et al. |
| 2004/0185011 A1 | 9/2004 | Alexander |
| 2005/0152851 A1 | 7/2005 | Kaminski |
| 2006/0024245 A1 | 2/2006 | Gebreselassie et al. |
| 2009/0155190 A1 | 6/2009 | Gebreselassie et al. |
| 2010/0061941 A1 | 3/2010 | Gebreselassie |
| 2011/0027328 A1 | 2/2011 | Baig et al. |
| 2011/0053826 A1 | 3/2011 | Wise |
| 2011/0262507 A1 | 10/2011 | Spring |
| 2013/0111682 A1 | 5/2013 | Pung |
| 2013/0302385 A1 | 11/2013 | Muenz et al. |
| 2014/0289984 A1 | 10/2014 | Vetter |
| 2015/0196185 A1 | 7/2015 | Fiske |
| 2015/0313803 A1 | 11/2015 | Lynch et al. |
| 2015/0313808 A1 | 11/2015 | Lynch et al. |
| 2016/0051684 A1 | 2/2016 | Wang |
| 2016/0120771 A1 | 5/2016 | Simonet et al. |
| 2016/0346175 A1 | 12/2016 | Sasik et al. |
| 2018/0127692 A1 | 5/2018 | Coope-epstein et al. |
| 2019/0160022 A1 | 5/2019 | Chiou |
| 2019/0298625 A1 | 10/2019 | Hilliard, Jr. et al. |
| 2019/0343732 A1 | 11/2019 | Mao |
| 2020/0000693 A1 | 1/2020 | Traynor et al. |
| 2021/0007940 A1 | 1/2021 | Swartz et al. |

FOREIGN PATENT DOCUMENTS

| | | |
|---|---|---|
| DE | 202007001353 U1 | 5/2007 |
| EP | 0916722 A2 | 5/1999 |
| EP | 2465487 A2 | 6/2012 |
| EP | 2170257 B1 | 11/2012 |
| GB | 2221389 A | 2/1990 |
| WO | 9209679 A1 | 6/1992 |
| WO | 0196461 A1 | 12/2001 |
| WO | 03075735 A1 | 9/2003 |
| WO | 2007133265 A2 | 11/2007 |
| WO | 2009095891 A1 | 8/2009 |
| WO | 2010060653 A2 | 6/2010 |
| WO | 2014124066 A1 | 8/2014 |

OTHER PUBLICATIONS

All Office Actions; U.S. Appl. No. 17/485,906, filed Sep. 27, 2021.
U.S. Appl. No. 17/485,906, filed Sep. 27, 2021, to first inventor et al.
All Office Actions; U.S. Appl. No. 18/450,176, filed Aug. 15, 2023.
U.S. Appl. No. 18/450,176, filed Aug. 15, 2023, to Matthew Lawrence Lynch et al.
All Office Actions, U.S. Appl. No. 17/196,379, filed Mar. 9, 2021.
All Office Actions, U.S. Appl. No. 17/225,146, filed Apr. 8, 2021.
All Office Actions, U.S. Appl. No. 17/225,148, filed Apr. 8, 2021.
All Office Actions, U.S. Appl. No. 17/225,149, filed Apr. 8, 2021.
All Office Actions, U.S. Appl. No. 17/225,150, filed Apr. 8, 2021.
All Office Actions, U.S. Appl. No. 17/225,151, filed Apr. 8, 2021.
All Office Actions, U.S. Appl. No. 17/225,153, filed Apr. 8, 2021.
All Office Actions, U.S. Appl. No. 17/225,176, filed Apr. 8, 2021.
All Office Actions, U.S. Appl. No. 17/225,218, filed Apr. 8, 2021.
Clinton D. Stevenson, et al. , "Capillary Pressure as Related to Water Holding in Polyacrylamide and Chicken Protein Gels", Journal of Food Science, vol. 78, Nr. 2, dated 2013,pp. C145-C151.
F. V. Ryer, Oil & Soap, "Research Laboratory, Lever Brothers Company Cambridge, Massachusetts", dated Oct. 1946, pp. 310-313.
F. V. Ryer, et al. Growing Single Crystals, "A Method of Growing Single Crystals Of Sodium Stearate And Sodium Palmitate", dated Feb. 4, 1944, pp. 154-158.
Marc N. G. de Mul, et al. Langmuir 2000, "Solution Phase Behavior and Solid Phase Structure of Long-Chain Sodium Soap Mixtures", vol. 16, No. 22, dated 2000, pp. 8276-8284.
Masao Sambuichi, et al. Dewatering Of Gels, "Filtration, Food Chemical Engineering, Solid Liquid Separation, Dewatering, Expression, Gel", Journal of Chemical Engineering of Japan, vol. 27, No. 5, dated 1994, pp. 616-620.
Matthew L Lynch, Acid-soaps, "The study of acid-soap crystals has resulted in many conflicting data", Current Opinion in Colloid & Interface Science, dated 1997,pp. 495-500.
Matthew L. Lynch, et al. Acid-soap crystals, "Spectroscopic and Thermal Characterization of 1:2 Sodium Soap/Fatty Acid Acid-Soap Crystals", J. Phys. Chem., vol. 100, No. 1, 1996, pp. 357-361.
Matthew L. Lynch, Structure of Fatty Acid-Soap Crystals, "Intermolecular Interactions and the Structure of Fatty Acid-Soap Crystals", J. Phys. Chem. B, vol. 105, No. 2, dated 2001, pp. 552-561.
Theodore P. Labuza, et al. , "Measurement Of Gel Water-Binding Capacity By Capillary Suction Potential", Journal of Food Science, vol. 43, dated 1978 ,pp. 1264-1269.

(56) References Cited

OTHER PUBLICATIONS

U.S. Appl. No. 17/196,379, filed Mar. 9, 2021, to first inventor Geoffrey Marc Wise.
U.S. Appl. No. 17/225,150, filed Apr. 8, 2021, to first inventor Matthew Lawrence Lynch et al.
U.S. Appl. No. 17/225,218, filed Apr. 8, 2021, to first inventor Matthew Lawrence Lynch et al.
U.S. Appl. No. 17/225,149, filed Apr. 8, 2021, to first inventor Matthew Lawrence Lynch et al.
U.S. Appl. No. 17/225,151, filed Apr. 8, 2021, to first inventor Matthew Lawrence Lynch et al.
U.S. Appl. No. 17/225,153, filed Apr. 8, 2021, to first inventor Matthew Lawrence Lynch et al.
U.S. Appl. No. 17/225,176, filed Apr. 8, 2021, to first inventor Matthew Lawrence Lynch et al.
U.S. Appl. No. 17/225,148, filed Apr. 8, 2021, to first inventor Matthew Lawrence Lynch et al.
Robert B Saper et al., "An Essential Micronutrient", vol. 79, No. 9, dated May 1, 2009, pp. 768-772.

\* cited by examiner

RHEOLOGICAL SOLID COMPOSITION

FIELD OF THE INVENTION

Rheological solid composition comprising more than about 80% water having a crystallizing agent with an elongated, fiber-like crystal habit. Wherein the rheological solid composition allows for a unique skin feel "crunch" and/or glide when rubbed on the skin providing an enhanced evaporative cooling for a refreshing/cooling sensation, even in the absence of sensate, and a low residue on skin; and wherein the rheological solid also exhibits properties of sufficient firmness, aqueous phase expression, and thermal stability critical for practical commercial viability.

BACKGROUND OF THE INVENTION

Conventional high-water containing compositions, such as rheological solid compositions, lack one or more desirable properties, for example low skin residue, sufficient firmness, aqueous phase expression, and thermal stability, particularly those comprising sodium carboxylate-based crystallizing agents. For instance, to produce a firm rheological solid composition using sodium stearate (C18) as a gelling agent in conventional soap-type deodorant gel-sticks requires the inclusion of high levels of polyols (e.g. propylene glycol and glycerin), as a solubility aid for the sodium stearate during processing, even at high process temperatures. Typical compositions include about 50% propylene glycol, 25% glycerin and only 25% water (EP2170257 and EP2465487). However, the addition of these processing aids eliminates the crunch and mutes the glide feel and cooling sensation of the solid gel stick. Even using lower amounts of a polyol compound, such as a glycol or a polyglycol, about 4% or more of sodium stearate (C18) is needed to provide sufficient firmness which then can result in higher amounts of gelling agent being left on the skin (U.S. Pat. No. 4,322,400). Traditional soap bars are comprised of similar gelling agents, but are far too concentrated in sodium carboxylate to effectively allow for aqueous phase expression with compression. Thermal stability is compromised in compositions when a gelling agent that is too soluble is added, as described in U.S. Pat. No. 5,340,492; in this instance, the thermal stability temperature of the composition is too low to effectively survive reliably on the shelf life or in the supply chain.

What is needed is a rheological solid composition that leaves little residue and has sufficient firmness, aqueous phase expression, and thermal stability. The present invention of a self-supporting structure comprising a crystalline mesh of a relatively rigid, framework of fiber-like crystalline particles, which if compressed, provides the properties of low residue, sufficient firmness, thermal stability, and aqueous phase expression.

SUMMARY OF THE INVENTION

A rheological solid composition is provided that comprises crystallizing agent and aqueous phase; wherein, the rheological solid composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m-3 to about 8,000 J m-3 as determined by the AQUEOUS PHASE EXPRESSION TEST METHOD; and wherein the crystallizing agent is a salt of fatty acids containing from about 13 to about 17 carbon atoms.

A method of producing a rheological solid composition is provided that comprises providing water; providing a crystallizing agent that is a salt of fatty acids containing from about 13 to about 17 carbon atoms; providing NaCl; wherein the NaCl is about 10% or less per weight percentage of the rheological solid composition; mixing the water, crystallizing agent, and NaCl; producing a rheological solid composition wherein, the rheological solid composition, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

A method of producing a rheological solid composition is provided that comprises providing water; providing a crystallizing agent that is a salt of fatty acids containing from about 13 to about 17 carbon atoms; mixing the water and crystallizing agent to produce a rheological solid composition; adding NaCl to the rheological solid composition; wherein, the rheological solid composition after addition of the NaCl, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

A rheological solid composition is provided that comprises crystallizing agent and aqueous phase; wherein, the rheological solid composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m-3 to about 8,000 J m-3 as determined by the AQUEOUS PHASE EXPRESSION TEST METHOD; and wherein the crystallizing agent is a salt of fatty acids containing from about 13 to about 16 carbon atoms.

A method of producing a rheological solid composition is provided that comprises providing water; providing a crystallizing agent that is a salt of fatty acids containing from about 13 to about 16 carbon atoms; providing NaCl; wherein the NaCl is about 10% or less per weight percentage of the rheological solid composition; mixing the water, crystallizing agent, and NaCl; producing a rheological solid composition wherein, the rheological solid composition, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

A method of producing a rheological solid composition is provided that comprises providing water; providing a crystallizing agent that is a salt of fatty acids containing from about 13 to about 16 carbon atoms; mixing the water and crystallizing agent to produce a rheological solid composition; adding NaCl to the rheological solid composition; wherein, the rheological solid composition after addition of the NaCl, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

The present invention includes a rheological solid composition comprising a crystalline mesh. The crystalline mesh ("mesh") comprises a relatively rigid, three-dimensional, interlocking crystalline skeleton framework of fiber-like crystalline particles (formed from crystallizing agents), having voids or openings containing aqueous solution and optionally one or more actives. The mesh provides a self-supporting structure, such that a rheological solid composition may 'stand on its own' when resting on a surface. If compressed above a critical stress, the mesh allows the rheological solid composition to express the entrapped aqueous phase, and optionally water soluble actives. The rheological solid compositions of the present invention include crystallizing agent(s), aqueous phase, and optionally active and may be combined with a device to enable application.

Figure 3:
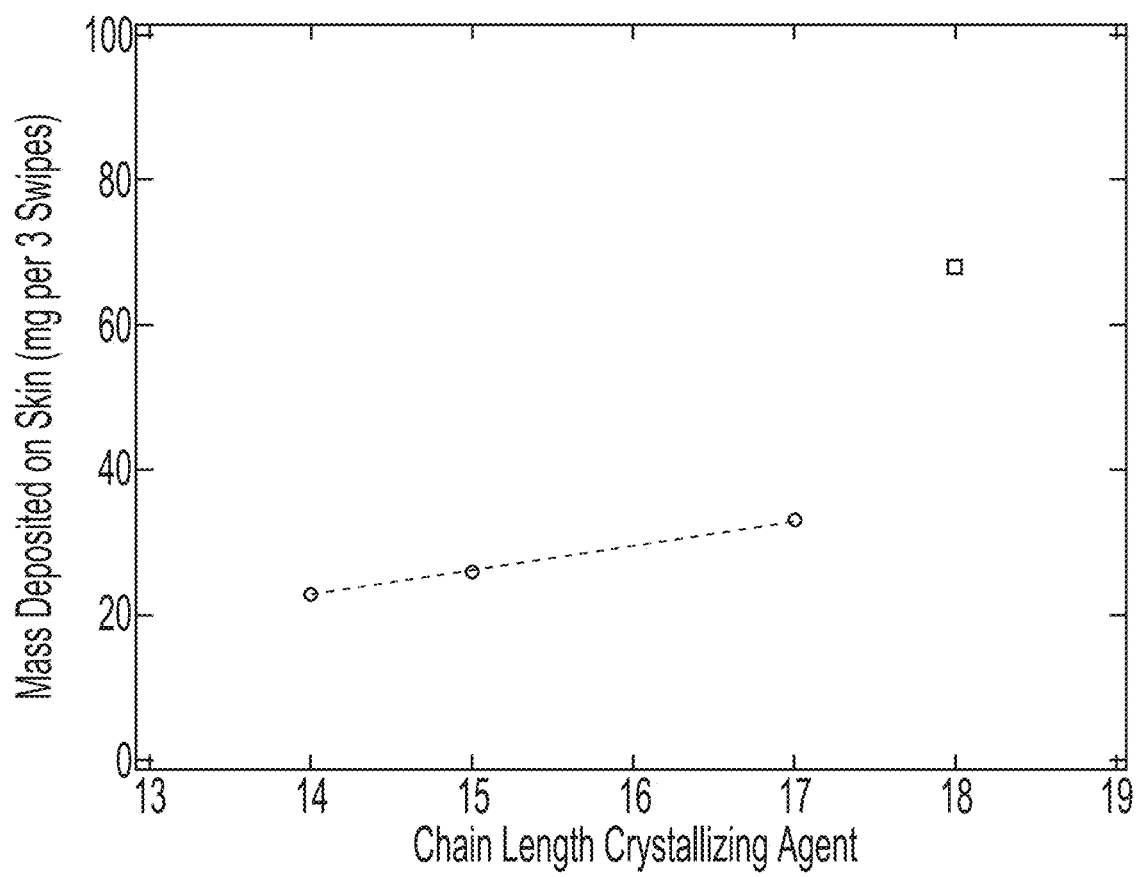

It is surprising that it is possible to prepare rheological solid compositions that exhibit low residue, sufficient firmness, aqueous phase expression, and thermal stability. Not wishing to be bound by theory, it is believed that sodium carboxylates of a sufficiently low chain length, such as from C13 to C17, present in high-water compositions (e.g. above about 80%), with the correct chain length purity and prepared under viable and practical process condition may form elongated, fiber-like crystal habits making these compositions particularly useful. These molecules have an ideal hydrophilic-hydrophobic balance between the head group and fatty chain to grow optimal crystal habits; these molecules also have a Krafft Temperature significantly below the viable and practical process temperatures, to grow optimal crystal habits. As compared to sodium carboxylates with longer chain lengths, such as C18, C19 and C20, shorter chain sodium carboxylates (C13 to C17) result in rheological solid compositions comprising a crystalline mesh, even at very low concentrations of sodium carboxylates, that are firm (resistant to compression stress) and deposit very little residual solid material upon a surface contacted by the rheological solid (resistant to shear stress) (FIG. 3). Firmness may be achieved by carefully adjusting the concentration and chain length distribution of the crystallizing agent.

Aqueous phase expression may be achieved from these rheological solid structures, by compression above a yield behavior that breaks the mesh structure allowing the water to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize until heated above 40° C. This is an important property in relation to the shelf-life and supply chain for consumer products. Addition of sodium chloride can be used to increase the thermal stability of the composition but should be added correctly to ensure the proper formation of the supporting mesh. These discovered design elements stand in contrast to compositions prepared with too-soluble a gelling agent to be practically thermal stable. Finally, in embodiments rheological solid compositions are prepared by cooling the mixture largely quiescently, in contrast to freezer or other mechanically invasive processes. Not wishing to be bound by theory, quiescent processes allow the formation of very large and efficient fibrous crystals rather than smaller less efficient crystals that are particularly subject to residual solid material deposition during use.

Crystallizing Agent(s)

Figure 1:
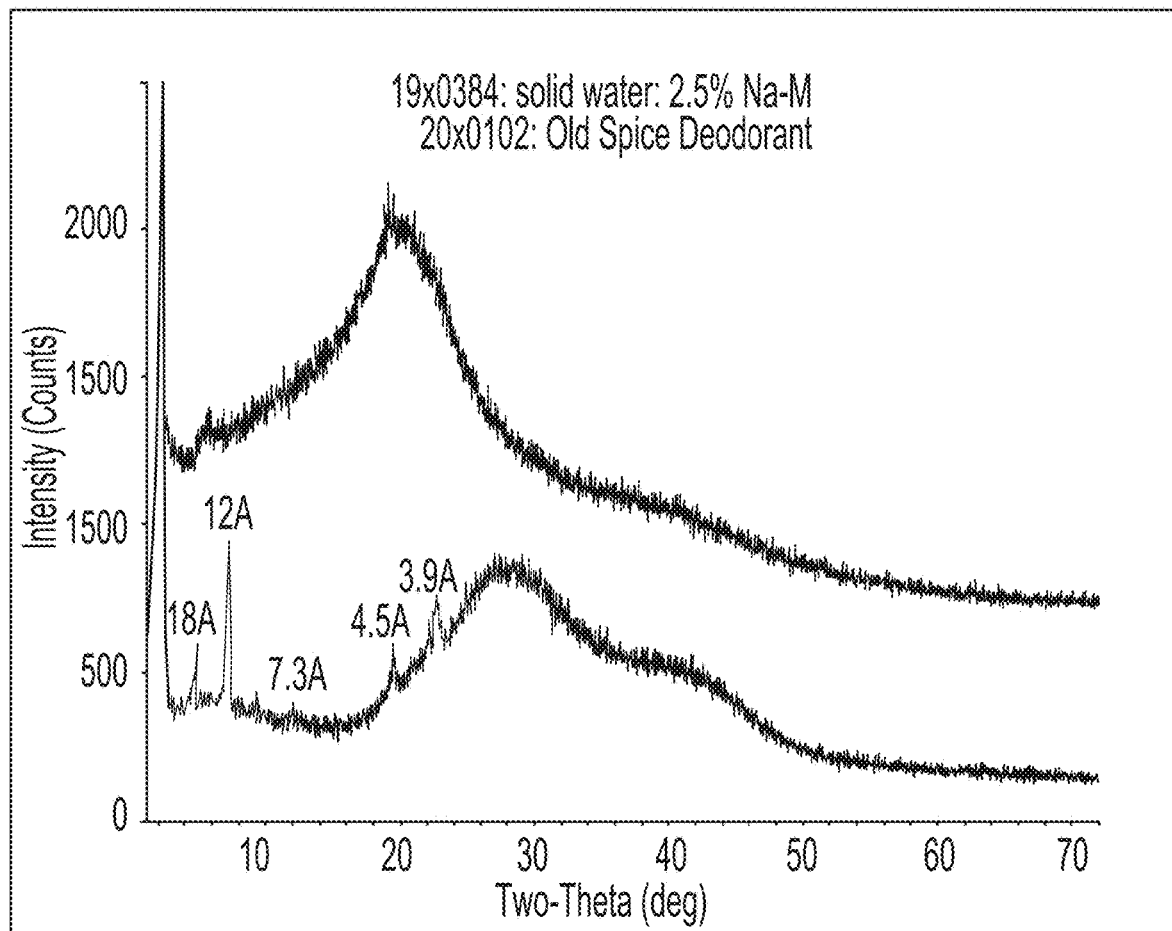
FIG. 1. X-ray Diffraction Pattern
FIG. 2. SEM of Interlocking Mesh
FIG. 3. Graph illustrating Composition Transferred to Skin.

In the present invention the mesh of a rheological solid composition includes fiber-like crystalline particles formed from crystallizing agents; wherein "crystallizing agent" as used herein includes sodium salts of fatty acid with shorter chain length (from about C13 to about C17 or from about C13 to about C16 or from about C13 to about C14), such as sodium tridecanoate, sodium pentadecanoate, sodium heptadecanoate, or sodium myristate (C14). Commercial sources of crystallizing agent usually comprise complicated mixtures of molecules, often with chain lengths between C10 to C22. The rheological solid compositions are best achieved with a 'narrow blend'—or distribution of crystallizing agent chain lengths, further best achieved with blends in the absence of very short chain lengths (C12 or shorter) and measurable amounts of unsaturation on the chains of the fatty acid sodium salts, and best achieved with a single chain length between C13 to C17, coupled with controlled crystallizing processing. Accordingly, rheological solid compositions are best achieved when the blend of the chain length distribution is preferably greater than about Po>0.3, more preferably about Po>0.5, more preferably about Po>0.6, more preferably about Po>0.7 and most preferably about Po>0.8, as determined by the BLEND TEST METHOD. One skilled in the art, recognizes crystalline particles as exhibiting sharp scattering peaks between 0.25-60 deg. 2θ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
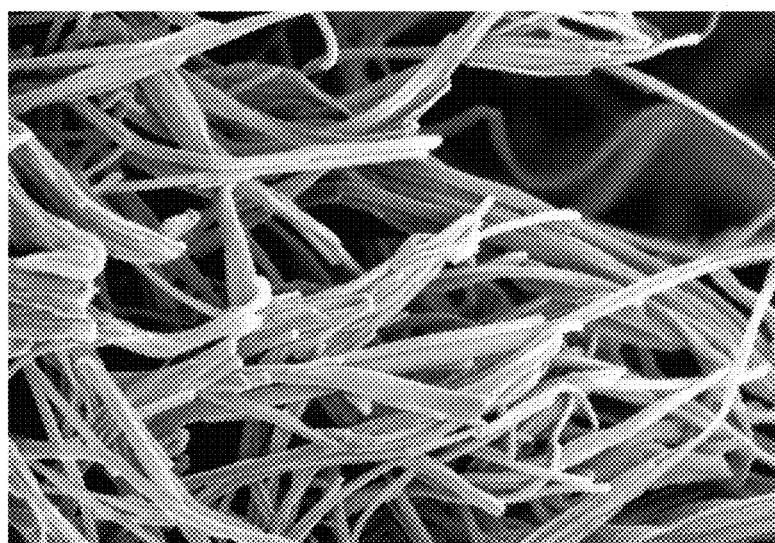

Rheological solid compositions comprise greater than about 80% water and are 'structured' by a mesh of interlocking, fiber-like crystalline particles of mostly single-chain length, as described above, see (FIG. 2). The term 'fiber-like crystalline particle' refers to a particle in which the length of the particle in the direction of its longest axis is greater than 10× the length of the particle in any orthogonal direction. The fiber-like crystalline particles produce a mesh at very low concentrations (~0.5 wt %) which creates a solid that yields only with a minimum applied stress—i.e. rheological solid. The aqueous phase primarily resides in the open spaces of the mesh. In preparing these compositions, the crystallizing agent is dissolved in aqueous phase using heat. The fiber-like crystalline particles form into the mesh as the mixture cools over minutes to hours.

Such compositions exhibit three properties used to make effective consumer product for envisioned applications:

Aqueous Phase Expression

Aqueous phase expression is an important property for consumer applications in the present invention, expressed in work to express water per unit volume, where preferred compositions are between 300 J m-3 and about 9,000 J m-3, more preferably between 1,000 J m-3 and about 8,000 J m-3, more preferably between 2,000 J m-3 and about 7,000 J m-3 and most preferably between 2,500 J m-3 and about 6,000 J m-3, as determined by the AQUEOUS PHASE EXPRESSION TEST METHOD. These limits allow for viable product compositions that—for example, provide evaporative and/or sensate-based cooling when the composition is applied to the skin and cleaning when applied to a hard surface. These work limits are in contrast to bar soaps and deodorant sticks that do not express aqueous phase when compressed. These work limits are also in contrast to gelatins that likewise do not express water when compressed. So, it is surprising that high-water compositions can be created with these materials that express aqueous phase with compression. Not wishing to be bound by theory, it is believed this a result of a network of crystalline materials that break up during the application of sufficient stress—releasing the aqueous phase with no uptake when the compression is released.

Firmness

Firmness should be agreeable to consumer applications, in forming a structured rheological solid composition, with preferred embodiments between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as a rheological solid stick to provide a dry-to-the-touch but wet-to-the-push properties. The firmness values are significantly softer than bar soaps and deodorants, which exceed these values. So, it is surprising that high-water compositions can be created that remain as rheological solid compositions with between about 0.25 wt % to about 10 wt % crystallizing agent, more preferably between about 0.5 wt % to about 7 wt % crystallizing agent and most preferably between about 1 wt % to about 5 wt % crystallizing agent. Not wishing to be bound by theory, it is believed this a result of crystallizing agent materials creating the interlocking mesh that provides sufficient firmness.

Thermal Stability

Thermal stability is used to ensure that the structured rheological solid composition can be delivered as intended to the consumer through the supply chain, preferably with thermal stability greater than about 40° C., more preferably greater than about 45° C., and most preferably greater than about 50° C., as determined by the THERMAL STABILITY TEST METHOD. Creating compositions with acceptable thermal stability is difficult, as it may vary unpredictably with concentration of the crystallizing agent and soluble active agent(s). Not wishing to be bound by theory, thermal stability results from the insolubility of the crystallizing agent in the aqueous phase. Conversely, thermal instability is thought to result from complete solubilization of the crystallizing agent that comprised the mesh.

Chain Length Blends

Effective chain length blends allow the creation of effective mesh microstructures in rheological solid compositions. In fact, adhoc (or informed selection) of crystallizing agents often leads to liquid or very soft compositions. The crystallizing agent may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—or the quantitative weight fraction of each chain length in the crystallizing agent, can be determined by the BLEND TEST METHOD, as described below. Commercial sources of crystallizing agent usually comprise complicated mixtures of molecules, often with chain lengths between 10 to 22.

Rheological solid compositions of the present invention have preferred chain length blends, as described by 'Optimal Purity' (Po) and 'Single Purity' (Ps), determined by the BLEND TEST METHOD. Sodium carboxylate crystallizing agents can have an 'Optimal Chain Length' of between 13 to 17 carbons and can be used alone or combined to form mesh structures that satisfy all three performance criteria of a rheological solid composition. Not wishing to be bound by theory, it is believed that these chain length molecules (13 to 17) have an optimal hydrophilic-hydrophobic balance and a solubilization temperature (e.g. Krafft Temperature) sufficiently below a viable and practical process temperature, that they can pack into crystals efficiently. Sodium carboxylate crystallizing agents having 'Unsuitable Chain Length' have chain lengths of sodium carboxylate molecules of 10, 12, 18:1 and 18:2 (i.e. shorter or unsaturated chain lengths). When present in compositions alone or in some combinations with 'optimal chain length' molecules, they do not form rheological solid composition that meet the required performance criteria. Accordingly, inventive compositions should have the proper purity of crystallizing agent molecules, to ensure the proper properties of the rheological solid composition. Po describes the total weight fraction of optimal chain length molecules of crystallizing agent to the total weight of crystallizing agent molecules, that is preferably Po>0.4, more preferably Po>0.6, more preferably Po>0.8 and most preferably Po>0.90. Ps describes the total weight fraction of the most common chain length molecule in the crystallizing agent to the total weight of crystallizing agent, that is preferably Ps>0.5, more preferably Ps>0.6, more preferably Ps>0.7, more preferably Ps>0.9.

Aqueous Phase

The rheological solid composition may include an aqueous carrier. The aqueous carrier which is used may be distilled, deionized, or tap water. Water may be present in any amount for the rheological solid composition to be an aqueous solution. Water may be present in an amount of about 80 wt % to 99.5 wt %, alternatively about 90 wt % to about 99.5 wt %, alternatively about 92 wt % to about 99.5 wt %, alternatively about 95 wt %, by weight of the rheological solid composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the rheological solid composition due to the addition of these alcohols to such things as perfumes and as stabilizers for some preservatives, the level of monohydric alcohol may about 1 wt % to about 5 wt %, alternatively less than about 6 wt %, alternatively less than about 3 wt %, alternatively less than about 1 wt %, by weight of the rheological solid composition.

However, other components can be optionally dissolved with the low molecular weight monohydric alcohols in the water to create an aqueous phase. Combined, these components are referred to as soluble active agents. Such soluble active agents include, but are not limited to, catalysts, activators, peroxides, enzymes, antimicrobial agents, preservatives, sodium chloride, surfactants and polyols. The crystallizing agent and insoluble active agents may be dispersed in the aqueous phase.

Catalysts

In embodiments, soluble active agents can include one or more metal catalysts. In embodiments, the metal catalyst can include one or more of dichloro-1,4-diethyl-1,4,8,11-tetraaazabicyclo[6.6.2]hexadecane manganese(II); and dichloro-1,4-dimethyl-1,4,8,11-tetraaazabicyclo[6.6.2] hexadecane manganese(II). In embodiments, the non-metal catalyst can include one or more of 2-[3-[(2-hexyldodecyl)oxy]-2-(sulfooxy)propyl]-3,4-dihydroisoquinolinium, inner salt; 3,4-dihydro-2-[3-[(2-pentylundecyl)oxy]-2-(sulfooxy) propyl]isoquinolinium, inner salt; 2-[3-[(2-butyldecyl)oxy]-2-(sulfooxy)propyl]-3,4-dihydroisoquinolinium, inner salt; 3,4-dihydro-2-[3-(octadecyloxy)-2-(sulfooxy)propyl]isoquinolinium, inner salt; 2-[3-(hexadecyloxy)-2-(sulfooxy) propyl]-3,4-dihydroisoquinolinium, inner salt; 3,4-dihydro-2-[2-(sulfooxy)-3-(tetradecyloxy)propyl]isoquinolinium, inner salt; 2-[3-(dodecyloxy)-2-(sulfooxy)propyl]-3,4-dihydroisoquinolinium, inner salt; 2-[3-[(3-hexyldecyl)oxy]-2-(sulfooxy)propyl]-3,4-dihydroisoquinolinium, inner salt; 3,4-dihydro-2-[3-[(2-pentylnonyl)oxy]-2-(sulfooxy)propyl] isoquinolinium, inner salt; 3,4-dihydro-2-[3-[(2-propylheptyl)oxy]-2-(sulfooxy)propyl]isoquinolinium, inner salt; 2-[3-[(2-butyloctyl)oxy]-2-(sulfooxy)propyl]-3,4-dihydroisoquinolinium, inner salt; 2-[3-(decyloxy)-2-(sulfooxy) propyl]-3,4-dihydroisoquinolinium, inner salt; 3,4-dihydro-2-[3-(octyloxy)-2-(sulfooxy)propyl]isoquinolinium, inner salt; and 2-[3-[(2-ethylhexyl)oxy]-2-(sulfooxy)propyl]-3,4-dihydroisoquinolinium, inner salt.

Activators

In embodiments, soluble active agent can include one or more activators. In embodiments, the activator can include one or more of tetraacetyl ethylene diamine (TAED); benzoylcaprolactam (BzCL); 4-nitrobenzoylcaprolactam; 3-chlorobenzoylcaprolactam; benzoyloxybenzenesulphonate (BOBS); nonanoyloxybenzene¬sulphonate (NOBS); phenyl benzoate (PhBz); decanoyloxybenzenesulphonate ($C_{10}$—OBS); benzoylvalerolactam (BZVL); octanoyloxybenzenesulphonate ($C_8$—OBS); perhydrolyzable esters; 4-[N-(nonaoyl) amino hexanoyloxy]-benzene sulfonate sodium salt. (NACA-OBS); dodecanoyloxybenzenesulphonate (LOBS or $C_{12}$—OBS); 10-undecenoyloxybenzenesulfonate (UDOBS or $C_{11}$—OBS with unsaturation in the 10 position); decanoyloxybenzoic acid (DOBA); (6-oclanamidocaproyl)oxybenzenesulfonate; (6-nonanamidocaproyl) oxybenzenesulfonate; and (6-decanamidocaproyl)oxybenzenesulfonate, Peroxy-Carboxylic Acids In embodiments, soluble active agent can include one or more preformed peroxy carboxylic acids. In embodiments, the peroxy carboxylic acids can include one or more of peroxymonosulfuric acids; perimidic acids; percabonic acids; percarhoxilic acids and salts of said acids; phthalimidoperoxyhexanoic acid; amidoperoxyacids; 1,12-diperoxydodecanedioic acid; and monoperoxyphthalic acid (magnesium salt hexahydrate), wherein said amidoperoxyacids may include N,N-terephthaloyl-di(6-aminocaproic acid), a monononylamide of either peroxysuccinic acid (NAPSA) or of peroxyadipic acid (NAPAA), or N-nonanoylaminoperoxycaproic acid (NAPCA).

In embodiments, water-based and/or water soluble benefit agent can include one or more diacyl peroxide. In embodiments, the diacyl peroxide can include one or more of dinonanoyl peroxide, didecanoyl peroxide, diundecanoyl peroxide, dilauroyl peroxide, and dibenzoyl peroxide, di-(3, 5,5-trimethyl hexanoyl) peroxide, wherein said diacyl peroxide can be clatharated.

Peroxides

In embodiments, soluble active agent can include one or more hydrogen peroxide. In embodiments, hydrogen peroxide source can include one or more of a perborate, a percarbonate a peroxyhydrate, a peroxide, a persulfate and mixtures thereof, in one aspect said hydrogen peroxide source may comprise sodium perborate, in one aspect said sodium perborate may comprise a mono- or tetra-hydrate, sodium pyrophosphate peroxyhydrate, urea peroxyhydrate, trisodium phosphate peroxyhydrate, and sodium peroxide.

Enzymes

In embodiments, soluble active agent can include one or more enzymes. In embodiment, the enzyme can include one or more of peroxidases, proteases, lipases, phospholipases, cellulases, cellobiohydrolases, cellobiose dehydrogenases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccases, amylases, and dnases.

Sensate

In embodiments, soluble active agent can include one or more components that provide a sensory benefit, often called a sensate. Sensates can have sensory attributes such as a warming, tingling, or cooling sensation. Suitable sensates include, for example, menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal known as CGA, Winsense WS-5 supplied by Renessenz-Symrise, Vanillyl butyl ether known as VBE, and mixtures thereof.

In certain embodiments, the sensate comprises a coolant. The coolant can be any of a wide variety of materials. Included among such materials are carboxamides, menthol, ketals, diols, and mixtures thereof. Some examples of carboxamide coolants include, for example, paramenthan carboxyamide agents such as N-ethyl-p-menthan-3-carboxamide, known commercially as "WS-3", N,2,3-trimethyl-2-isopropylbutanamide, known as "WS-23," and N-(4-cyanomethylphenyl)-ρ-menthanecarboxamide, known as G-180 and supplied by Givaudan. G-180 generally comes as a 7.5% solution in a flavor oil, such as spearmint oil or peppermint oil. Examples of menthol coolants include, for example, menthol; 3-1-menthoxypropane-1,2-diol known as TK-10, manufactured by Takasago; menthone glycerol acetal known as MGA manufactured by Haarmann and Reimer; and menthyl lactate known as Frescolat® manufactured by Haarmann and Reimer. The terms menthol and menthyl as used herein include dextro- and levorotatory isomers of these compounds and racemic mixtures thereof.

In certain embodiments, the sensate comprises a coolant selected from the group consisting of menthol; 3-1-menthoxypropane-1,2-diol, menthyl lactate; N,2,3-trimethyl-2-isopropylbutanamide; N-ethyl-ρ-menthan-3-carboxamide;

N-(4-cyanomethylphenyl)-ρ-menthanecarboxamide, and combinations thereof. In further embodiments, the sensate comprises menthol; N,2,3-trimethyl-2-isopropylbutanamide.

Surfactant

Detersive Surfactant: Suitable detersive surfactants include anionic detersive surfactants, non-ionic detersive surfactant, cationic detersive surfactants, zwitterionic detersive surfactants and amphoteric detersive surfactants and mixtures thereof. Suitable detersive surfactants may be linear or branched, substituted or un-substituted, and may be derived from petrochemical material or biomaterial. Preferred surfactant systems comprise both anionic and non-ionic surfactant, preferably in weight ratios from 90:1 to 1:90. In some instances a weight ratio of anionic to nonionic surfactant of at least 1:1 is preferred. However, a ratio below 10:1 may be preferred. When present, the total surfactant level is preferably from 0.1% to 60%, from 1% to 50% or even from 5% to 40% by weight of the subject composition.

Anionic detersive surfactant: Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C8-C22 alkyl, or acyl group. Such surfactants are employed in the form of water-soluble salts and the salt-forming cation usually is selected from sodium, potassium, ammonium, magnesium and triethanol amine, with the sodium cation being the usual one chosen.

Anionic surfactants of the present invention and adjunct anionic cosurfactants, may exist in an acid form, and said acid form may be neutralized to form a surfactant salt which is desirable for use in the present compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, oligamines, or alkanolamines. Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Suitable sulphonate detersive surfactants include methyl ester sulphonates, alpha olefin sulphonates, alkyl benzene sulphonates, especially alkyl benzene sulphonates, preferably $C_{10-13}$ alkyl benzene sulphonate. Suitable alkyl benzene sulphonate (LAS) is obtainable, preferably obtained, by sulphonating commercially available linear alkyl benzene (LAB). Suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used Suitable sulphate detersive surfactants include alkyl sulphate, preferably $C_{8-18}$ alkyl sulphate, or predominantly $C_{12}$ alkyl sulphate.

A preferred sulphate detersive surfactant is alkyl alkoxylated sulphate, preferably alkyl ethoxylated sulphate, preferably a $C_{8-18}$ alkyl alkoxylated sulphate, preferably a $C_{8-18}$ alkyl ethoxylated sulphate, preferably the alkyl alkoxylated sulphate has an average degree of alkoxylation of from 0.5 to 20, preferably from 0.5 to 10, preferably the alkyl alkoxylated sulphate is a C8-18 alkyl ethoxylated sulphate having an average degree of ethoxylation of from 0.5 to 10, preferably from 0.5 to 5, more preferably from 0.5 to 3. The alkyl alkoxylated sulfate may have a broad alkoxy distribution or a peaked alkoxy distribution.

The alkyl sulphate, alkyl alkoxylated sulphate and alkyl benzene sulphonates may be linear or branched, including 2 alkyl substituted or mid chain branched type, substituted or un-substituted, and may be derived from petrochemical material or biomaterial. Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the compositions of the invention. Most preferably the branched sulfated anionic surfactant is selected from alkyl sulfates, alkyl ethoxy sulfates, and mixtures thereof.

Alkyl sulfates and alkyl alkoxy sulfates are commercially available with a variety of chain lengths, ethoxylation and branching degrees. Commercially available sulfates include those based on Neodol alcohols ex the Shell company, Lial-Isalchem and Safol ex the Sasol company, natural alcohols ex The Procter & Gamble Chemicals company.

Other suitable anionic detersive surfactants include alkyl ether carboxylates.

Non-ionic detersive surfactant: Suitable non-ionic detersive surfactants are selected from the group consisting of: $C_8$-C18 alkyl ethoxylates, such as, NEODOL® non-ionic surfactants from Shell; $C_6$-C12 alkyl phenol alkoxylates wherein preferably the alkoxylate units are ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; alkylpolysaccharides, preferably alkylpolyglycosides; methyl ester ethoxylates; polyhydroxy fatty acid amides; ether capped poly(oxyalkylated) alcohol surfactants; and mixtures thereof.

Suitable non-ionic detersive surfactants are alkylpolyglucoside and/or an alkyl alkoxylated alcohol.

Suitable non-ionic detersive surfactants include alkyl alkoxylated alcohols, preferably $C_{8-18}$ alkyl alkoxylated alcohol, preferably a $C_{8-18}$ alkyl ethoxylated alcohol, preferably the alkyl alkoxylated alcohol has an average degree of alkoxylation of from 1 to 50, preferably from 1 to 30, or from 1 to 20, or from 1 to 10, preferably the alkyl alkoxylated alcohol is a $C_{8-18}$ alkyl ethoxylated alcohol having an average degree of ethoxylation of from 1 to 10, preferably from 1 to 7, more preferably from 1 to 5 and most preferably from 3 to 7. The alkyl alkoxylated alcohol can be linear or branched, and substituted or un-substituted. Suitable non-ionic surfactants include those with the trade name Lutensol® from BASF.

Cationic detersive surfactant: Suitable cationic detersive surfactants include alkyl pyridinium compounds, alkyl quaternary ammonium compounds, alkyl quaternary phosphonium compounds, alkyl ternary sulphonium compounds, and mixtures thereof.

Preferred cationic detersive surfactants are quaternary ammonium compounds having the general formula:

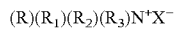

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, preferred anions include: halides, preferably chloride; sulphate; and sulphonate.

Amphoteric and Zwitterionic detersive surfactant: Suitable amphoteric or zwitterionic detersive surfactants include amine oxides, and/or betaines. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3)O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides.

Other suitable surfactants include betaines, such as alkyl betaines, alkylamidobetaine, amidazoliniumbetaine, sulfobetaine (INCI Sultaines) as well as Phosphobetaines Antimicrobial Compounds In embodiments, soluble active agent can include an effective amount of a compound for reducing the number of viable microbes in the air or on inanimate surfaces. Antimicrobial compounds are effective on gram negative or gram positive bacteria or fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. The antimicrobial compounds may also be effective at reducing the number of viable viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the rheological solid composition can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

A quaternary compound may be used. Examples of commercially available quaternary compounds suitable for use in the rheological solid composition are Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the rheological solid composition.

Preservatives

In embodiments, soluble active agent can include a preservative. The preservative may be present in an amount sufficient to prevent spoilage or prevent growth of inadvertently added microorganisms for a specific period of time, but not sufficient enough to contribute to the odor neutralizing performance of the rheological solid composition. In other words, the preservative is not being used as the antimicrobial compound to kill microorganisms on the surface onto which the rheological solid composition is deposited in order to eliminate odors produced by microorganisms. Instead, it is being used to prevent spoilage of the rheological solid composition in order to increase the shelf-life of the rheological solid composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation; 1,2-Benzisothiazolin-3-one; Acticide MBS.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the rheological solid composition.

Adjuvants

Adjuvants can be added to the rheological solid composition herein for their known purposes. Such adjuvants include, but are not limited to, water soluble metallic salts, including zinc salts, copper salts, and mixtures thereof;

antistatic agents; insect and moth repelling agents; colorants; antioxidants; aromatherapy agents and mixtures thereof.

The compositions of the present invention can also comprise any additive usually used in the field under consideration. For example, non-encapsulated pigments, film forming agents, dispersants, antioxidants, essential oils, preserving agents, fragrances, liposoluble polymers that are dispersible in the medium, fillers, neutralizing agents, silicone elastomers, cosmetic and dermatological oil-soluble active agents such as, for example, emollients, moisturizers, vitamins, anti-wrinkle agents, essential fatty acids, sunscreens, and mixtures thereof can be added.

Solvents

The composition can contain a solvent. Non-limiting examples of solvents can include ethanol, glycerol, propylene glycol, polyethylene glycol 400, polyethylene glycol 200, and mixtures thereof. In one example the composition comprises from about 0.5% to about 15% solvent, in another example from about 1.0% to about 10% solvent, and in another example from about 1.0% to about 8.0% solvent, and in another example from about 1% solvent to about 5% solvent.

Vitamins

As used herein, "xanthine compound" means one or more xanthines, derivatives thereof, and mixtures thereof. Xanthine Compounds that can be useful herein include, but are not limited to, caffeine, xanthine, 1-methyl xanthine, theophylline, theobromine, derivatives thereof, and mixtures thereof. Among these compounds, caffeine is preferred in view of its solubility in the composition. The composition can contain from about 0.059, preferably from about 2.0%, more preferably from about 0.1%, still more preferably from about 1.0%, and to about 0.2%, preferably to about 1.0%, more preferably to about 0.3% by weight of a xanthine compound As used herein, "vitamin B3 compound" means a one or more compounds having the formula:

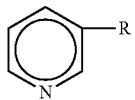

wherein R is —CONH$_2$ (i.e., niacinamide), —COOH (i.e., nicotinic acid) or —CH$_2$OH (i.e., nicotinyl alcohol), derivatives thereof; mixtures thereof; and salts of any of the foregoing.

Exemplary derivatives of the foregoing vitamin B3 compounds include nicotinic acid esters, including non-vasodilating esters of nicotinic acid (e.g, tocopherol nicotinate, and myristyl nicotinate), nicotinyl amino acids, nicotinyl alcohol esters of carboxylic acids, nicotinic acid N-oxide and niacinamide N-oxide. The composition can contain from about 0.05%, preferably from about 2.0%, more preferably from about 0.1%, still more preferably from about 1.0%, and to about 0.1%, preferably to about 0.5%, more preferably to about 0.3% by weight of a vitamin B3 compound As used herein, the term "panthenol compound" is broad enough to include panthenol, one or more pantothenic acid derivatives, and mixtures thereof. panthenol and its derivatives can include D-panthenol ([R]-2,4-dihydroxy-N-[3-hydroxypropyl)]3,3-dimethylbutamide), DL-panthenol, pantothenic acids and their salts, preferably the calcium salt, panthenyl triacetate, royal jelly, panthetine, pantotheine, panthenyl ethyl ether, pangamic acid, pantoyl lactose, vitamin B complex, or mixtures thereof. The composition can contain from about 0.01%, preferably from about 0.02%, more preferably from about 0.05%, and to about 3%, preferably to about 1%, more preferably to about 0.5% by weight of a panthenol compound Sodium chloride (and other sodium salts) is a particular useful additive to the aqueous phase to adjust the thermal stability of compositions but must be added into the composition with particular care (Example 3). Not wishing to be bound by theory, sodium chloride is thought to 'salt out' inventive crystallizing agents decreasing their solubility. This has the effect of increasing the thermal stability temperature of the rheological solid composition as measured by the THERMAL STABILITY TEST METHOD. For example, Optimal Chain Length crystallizing agents can have the thermal stability temperatures increased as much as 15° C. with sodium chloride addition. This is particularly valuable as the addition of other ingredients into the aqueous phase often lower the thermal stability temperature in the absence of sodium chloride. Surprisingly, adding sodium chloride can lead to adverse effects in the preparation of the rheological solid compositions. It is preferable in most making processes, to add sodium chloride into the hot crystallizing agent aqueous phase before cooling to form the mesh. However, adding too much may cause 'curding' of the crystallizing agents and absolutely horrid compositions. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the crystallizing agents, to form plates or platelet crystals, which are not rheological solids.

Rheological Solid Composition Properties

Stability Temperature

Stability temperature, as used herein, is the temperature at which most or all of the crystallizing agent completely dissolves into an aqueous phase, such that a composition no longer exhibits a stable solid structure and may be considered a liquid. In embodiments of the present invention the stability temperature range may be from about 40° C. to about 95° C., about 40° C. to about 90° C., about 50° C. to about 80° C., or from about 60° C. to about 70° C., as these temperatures are typical in a supply chain. Stability temperature can be determined using the THERMAL STABILITY TEST METHOD, as described below.

Firmness

Depending on the intended application, such as a stick, firmness of the composition may also be considered. The firmness of a composition may, for example, be expressed in Newtons of force. For example, compositions of the present invention comprising 1-3 wt % crystallizing agent may give values of about 4-about 12 N, in the form of a solid stick or coating on a sheet. As is evident, the firmness of the composition according to embodiments of the present invention may, for example, be such that the composition is advantageously self-supporting and can release liquids and/ or actives upon application of low to moderate force, for example upon contact with a surface, to form a satisfactory deposit on a surface, such as the skin and/or superficial body growths, such as keratinous fibers. In addition, this hardness may impart good impact strength to the inventive compositions, which may be molded or cast, for example, into stick or sheet form, such as a wipe product. The composition of the invention may also be transparent or clear, including for example, a composition without pigments. Preferred firmness is between about 0.1 N to about 50.0 N, more preferably between about 0.5 N to about 40.0 N, more preferably between about 1.0 N to about 30.0 N and most preferably between about 2.5 N to about 15.0 N. The firmness may be measured using the FIRMNESS TEST METHOD, as described below.

Aqueous Phase Expression

Depending on the intended application, such as a stick, aqueous phase expression of the composition may also be considered. This is a measure of the amount of work need per unit volume to express the aqueous phase from the compositions, with larger values meaning it becomes more difficult to express liquid. A low value might be preferred, for example, when applying the composition to the skin. A high value might be preferred, for example, when the composition is applied to a substrate that requires 'dry-to-the-touch-but-wet-to-the-wipe' properties. Preferred values are between about 100 J m-3 to about 8,000 J m-3, more preferably between about 1,000 J m-3 to about 7,000 J m-3, and most preferably between about 2,000 J m-3 to about 5,000 J m-3. The liquid expression may be measured using the AQUEOUS PHASE EXPRESSION TEST METHOD, as described herein.

Firmness Test Method

All samples and procedures are maintained at room temperature (25±3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-position so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD, are all entered in the examples in the row entitles 'Firmness'. In general, the numeric value is returned as the average of the maximum value of three measurements as described above, except in one of the two cases:
1) the composition does not form a homogenous rheological solid (e.g. completely or partially liquid), the value of 'NM1' is returned;
2) and, the composition curds during making, the value of 'NM2' is returned.

Thermal Stability Test Method

All samples and procedures are maintained at room temperature (25±3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent; Mettler Toledo, LLC., Columbus, OH). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC (TA Instruments, New Castle, DE) in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD, are all entered in the examples in the row entitles 'Temperature'. In general, the numeric value is returned as described above, except in one of the two cases:
1) the composition does not form a homogenous rheological solid (e.g. completely or partially liquid) and is not suitable for the measurement, the value of 'NM3' is returned;
2) and, the composition curds during making and is not suitable for the measurement, the value of 'NM4' is returned.

Aqueous Phase Expression Test Method

All samples and procedures are maintained at room temperature 25 (±3° C.) prior to testing.

Measurements for the determination of aqueous phase expression were made with a TA Discovery HR-2 Hybrid Rheometer (TA Instruments, New Castle, DE) and accompanying TRIOS software version 3.2.0.3877, or equivalent. The instrument is outfitted with a DHR Immobilization Cell (TA Instrument) and 50 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. It is critical that the sample be prepared in Speed Mixer containers (Flak-Tech, Max 60 Cup Translucent, Cat #501 222t), so that the diameter of the sample matches the diameter of the HR-2 Immobilization Cell. The sample is released from the containers by running a thin spatula between the edge of the container and the sample. The container is gently turned over and placed on a flat surface. A gentle force is applied to the center of the bottom of the overturned container, until the sample releases and gently glides out of the container. The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the aqueous phase to escape through the bottom of the sample. This also ensures that any change in the height of the sample for the experiment is equivalent to the amount of aqueous phase expressed during the test. At the end of the measurement, one should confirm that the aqueous phase is indeed expressed from the sample through the measurement, by looking for aqueous phase in the effluent tube connected to the Immobilization Cell. If no aqueous phase is observed, the sample is deemed not to express aqueous phase and is not inventive.

Set the instrument settings as follows. Select Axial Test Geometry. Then, set "Geometry" options: Diameter=50 mm; Gap=45000 um; Loading Gap=45000 um; Trim Gap Offset=50 um; Material='Steel'; Environmental System="Peltier Plate". Set "Procedure" options: Temperature=25° C.; Soak Time=0 sec; Duration=2000 sec; Motor Direction="Compression"; Constant Linear Rate=2 um sec-1; Maximum Gap Change=0 um; Torque=0 uN·m; Data Acquisition='save image' every 5 sec.

Manually move the steel tool within about 1000 um of the surface of the sample, taking care that the tool does not touch the surface. In the "Geometry" options, reset Gap to this distance.

Start the run.

The data is expressed in two plots:
1) Plot 1: Axial Force (N) on the left-y-axis and Step Time (s) on the x-axis;
2) Plot 2: Gap (um) on the right-y-axis and Step Time (s) on the x-axis.

The Contact Time—T (contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the aqueous phase from the structure is the area under the Axial Force curve in Plot 1 between T(contact) and T(compression) multiplied by Constant Linear Rate, or 2e-6 m s−1 normalized by dividing the total volume of expressed fluids, and is expressed in units of Joules per cubic meter (J m-3).

The results of the AQUEOUS PHASE EXPRESSION TEST METHOD, are all entered in the examples in the row entitled 'AP Expression'. In general, the numeric value, as the average of at least two values is returned as described, except in one of the four cases:
1) the composition does not form a homogenous rheological solid (e.g. completely or partially liquid) and is not suitable for the measurement, the value of 'NM5' is returned;
2) the composition curds during making and is not suitable for the measurement, the value of 'NM6' is returned;
3) the composition is a rheological solid but too soft to effectively load in the device, the value of 'NM7' is returned;
4) and the composition is too hard so that the force exceeds 50 N before the 15% compression, the value of 'NM8' is returned;

Blend Test Method

All samples and procedures are maintained at room temperature 25 (±3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent. A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hot plate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, CA), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250° C. for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the crystallizing agent is described in the following ways: Optimal Purity—Po, which is the mass fraction of the optimal chain length molecules in the crystallizing agent blend calculated as:

$$Po = \frac{\Sigma Mo}{Mt}$$

where Mo is the mass of each optimal chain length in the crystallizing agent and Mt is the total mass of the crystallizing agent.

Single Purity—Ps, which is the mass fraction of the most common chain length in the crystallizing agent blend calculated as:

$$Ps = \frac{Ms}{Mt}$$

where Ms is the mass of the most common chain length in the crystallizing agent and Mt is the total mass of the crystallizing agent. The value is expressed in brackets—[Ms], if the most common chain length is selected from the group of unsuitable chain length molecules.

EXAMPLES

Materials List
(1) Water: Millipore, Burlington, MA (18 m-ohm resistance)
(2) Sodium caprate (sodium decanoate, NaC10): TCI Chemicals, Cat #D0024
(3) Sodium laurate (sodium dodecanoate, NaC12): TCI Chemicals, Cat #D0024
(4) Sodium myristate (sodium tetradecanoate, NaC14): TCI Chemicals, Cat. #M0483
(5) Sodium palmitate (sodium hexadecanoate, NaC16): TCI Chemicals, Cat. #P0007
(6) Sodium stearate (sodium octadecanoate, NaC18): TCI Chemicals, Cat. #S0081
(7) Sodium oleate (sodium trans-9-octadecanoate, NaC18:1): TCI Chemicals, Cat #O0057
(8) Pentadecylic acid (pentadecanoic acid, HC15): TCI Chemicals, Cat #P0035
(9) Margaric acid (heptadecanoic acid, HC17): TCI Chemicals, Cat #H0019
(10) Nonadecylic acid (nonadecanoic acid, HC19): TCI Chemicals, Cat #N0283
(11) C1270 K ID: P&G Chemicals, Cincinnati, OH) prod. code 10275803
(12) C1618 K ID: P&G Chemicals, Cincinnati, OH) prod. code 10275805
(13) C1218 K ID: P&G Chemicals, Cincinnati, OH) prod. code 10275798
(14) C1214 K ID: P&G Chemicals, Cincinnati, OH) prod. code 10275796
(15) NaOH: 0.10 M, Fluka Chemical, Cat #319481-500ML
(16) Sodium chloride (NaCl): VWR, Cat #BDH9286-500G
(17) Lauric acid (HL): TCI Chemicals, Cat #L0011
(18) NaOH: 1.0 N, Honeywell/Fluka, Cat #35256-1L Example 1

These include samples containing crystallizing agents with a Po value of about 1 and Ps value of also about 1, as determined by the BLEND TEST METHOD, contrasting optimal and unsuitable crystallizing agents. Examples A-E (Tables 1-2) show samples prepared with different weight percentage of sodium tetradecanoate. The increasing concentrations increase both firmness and temperature stability of the samples, but also make it more difficult to express aqueous phase, as reflected in the aqueous phase expression value. As Example E shows—at about 9 wt %, it is no longer practical to express aqueous phase, as has been observed with soap bars that use these materials as gelling agents. Examples F-H (Table 2), show that other optimal chain length crystallizing agents, share similar trends as the previous examples. Example I-K (Table 3) have unsuitable crystallizing agents, and the sample compositions result in liquids. Not wishing to be bound by theory, it is believed these crystallizing agents are either too soluble (e.g. low Krafft Temperature) or 'kinks' from unsaturation in the chains disrupts crystallization. Examples L-N (Table 4) demonstrate that it is possible to create compositions with odd-chain length crystallizing agents. It is believed odd-chain-length crystallizing agents crystallize in a different manner than even chain-length crystallizing agents, so that it is surprising these compositions still form effective mesh structures.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples A-K were prepared by first adding Water (1; the number references the component's listing on the Material List) and crystallizing agent (2-7) to the beaker. The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples. Representative data demonstrates that the prototypes exhibit the required properties for these rheological solid compositions.

Examples L-N were prepared by first adding NaOH (15) and fatty acid (8-10) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml. The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples and blend was determined from the BLEND TEST METHOD. Representative data demonstrates that the prototypes exhibit the required properties of firmness, aqueous phase expression and thermal stability for these rheological solid compositions.

TABLE 1

|  | Sample A FG4005-7 Inventive | Sample B FG4005-8 Inventive | Sample C FG4005-9 Inventive | Sample D FG4005-10 Inventive |
|---|---|---|---|---|
| (1) Water | 99.501 g | 99.001 g | 97.001 g | 95.001 g |
| (2) NaC10 | — | — | — | — |
| (3) NaC12 | — | — | — | — |
| (4) NaC14 | 0.500 g | 1.003 g | 3.001 g | 5.003 g |
| (5) NaC16 | — | — | — | — |
| % Crystallizing Agent | 0.5 wt % | 1.0 wt % | 3.0 wt % | 5.0 wt % |
| Firmness | 0.51N | 1.24N | 8.65N | 14.31N |
| AP Expression | NM7 | 340 J m−3 | 6,260 J m−3 | 7,730 J m−3 |
| Temperature | 46.7° C. | 45.0° C. | 48.5° C. | 54.3° C. |
| Po | 1.00 | 1.00 | 1.00 | 1.00 |
| Ps | 1.00 | 1.00 | 1.00 | 1.00 |

TABLE 2

|  | Sample E FG4005-12 Comparative | Sample F FG4005-13 Inventive | Sample G FG4005-17 Inventive |
|---|---|---|---|
| (1) Water | 91.000 g | 99.501 g | 93.002 g |
| (2) NaC10 | — | — | — |
| (3) NaC12 | — | — | — |
| (4) NaC14 | 9.000 g | — | — |
| (5) NaC16 | — | 0.500 g | 7.002 g |
| % Crystallizing Agent | 9.0 wt % | 0.5 wt % | 7.0 wt % |
| Firmness | 40.92N | 0.51N | 5.03N |
| AP Expression | NM8 | NM7 | 2,550 J m−3 |
| Temperature | 56.4° C. | 59.0° C. | 64.3° C. |
| Po | 1.00 | 1.00 | 1.00 |
| Ps | 1.00 | 1.00 | 1.00 |

TABLE 3

|  | Sample I NB Comparative | Sample J 1531-32 Comparative | Sample K 1531-33 Comparative |
|---|---|---|---|
| (1) Water | 48.500 g | 48.611 g | 48.740 g |
| (2) NaC10 | 1.500 g | — | — |
| (3) NaC12 | — | 1.547 g | — |
| (4) NaC14 | — | — | — |
| (5) NaC16 | — | — | — |
| (6) NaC18 | — | — | — |
| (7) NaC18:1 | — | — | 1.505 g |
| % Crystallizing Agent | 3.0 wt % | 3.1 wt % | 3.0 wt % |
| Firmness | NM1 | NM1 | NM1 |
| AP Expression | NM5 | NM5 | NM5 |
| Temperature | NM3 | NM3 | NM3 |
| Po | 0.00 | 0.00 | 0.00 |
| Ps | [1.00] | [1.00] | [1.00] |

TABLE 4

|  | Sample L 1531-100 Inventive | Sample M 1531-101 Inventive | Sample N 1531-102 Comparative |
|---|---|---|---|
| (8) H C15 | — | 2.561 g | — |
| (9) H C17 | 2.761 g | — | — |
| (10) H C19 | — | — | 3.090 g |
| % Crystallizing Agent | 2.76 wt % | 2.56 wt % | 3.09 wt % |
| (15) NaOH | 97.210 g | 97.442 g | 96.911 g |
| Firmness | 8.10N | 4.49N | NM1 |
| AP Expression | 6,001 J m−3 | 3,688 J m−3 | — |
| Temperature | 75.2° C. | 63.0° C. | — |
| Po | 1.00 | 1.00 | 1.00 |
| Ps | 1.00 | 1.00 | 1.00 |

Example 2

This example includes compositions that contain blends of crystallizing agent molecules, as determined by the BLEND TEST METHOD, contrasting the effects of the relative amounts of optimal and unsuitable chain length crystallizing agent molecules on the three required properties. Examples O-R (Table 5) show samples prepared using different weight percentages of typical commercial fatty acid mixtures. The header shows the particular crystallizing agent used in the preparation and the 'from analysis' shows the chain length distribution from the BLEND TEST METHOD. All the compositions failed to crystallize and could not be measured for firmness, stability temperature or aqueous phase expression. Not wishing to be bound by theory, it is believed these samples have too high a level of unsuitable crystallizing agents to initiate viable mesh formation. Examples S-V (Table 6) show the effect of adjusting the comparative levels of optimal and unsuitable crystallizing agent chain length in the composition. While the weight percent of the crystallizing agent remains constant in the compositions, the amount of unsuitable chain length (C10) increases, resulting in the production of softer compositions having lower thermal stability temperature that do not crystallize to form a mesh structure. While the weight percent of the crystallizing agent remains constant in the compositions, the amount of unsuitable chain length (C10) increases resulting in the production of softer compositions, having lower thermal stability temperature that do not crystallize to form a mesh structure. Surprisingly, the effect of the unsuitable crystallizing agents is more detrimental in combination with the shorter chain length optimal crystallizing agent. Not wishing to be bound by theory, but it is believed that the fibrous crystals are 'held' together primarily by chain-to-chain interactions of the crystallizing agents in the crystals and, being fewer with shorter chain length crystallizing agents, are more susceptible to the presence of unsuitable crystallizing agents in the crystals.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples O-R were prepared by first adding NaOH (15) and commercial fatty acid (11-14) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml. They were cooled at room temperature 25 (±3° C.). These samples remained liquid and consequently were not measured for firmness, thermal stability or water expression. One skilled in art recognizes that cooling compositions of crystallizing agent at different rates may result in modest differences in the firmness, aqueous phase expression and stability temperature properties; this is common in samples prepared at different absolute weights.

Examples S-Z were prepared by first adding Water (1) and crystallizing agent (2-7) to the beaker. The beaker was placed on the heating-pad assembly. The overhead stirrer was placed in the beaker and set to rotate at 100 rpm. The heater was set at 70° C. The preparation was heated to 70° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Aqueous phase expression measurements were made by the AQUEOUS PHASE EXPRESSION TEST METHOD on the two 25 ml samples, in all cases except Example V and Example Z, which remained liquid. The blend was determined from the BLEND TEST METHOD.

One skilled in art recognizes that cooling compositions of crystallizing agent at different rates may result in modest differences in the firmness, aqueous phase expression and stability temperature properties; this is common in samples prepared at different absolute weights.

TABLE 5

|  | Sample O 1531-119 (11) C-1270 K Comparative | Sample P 1531-120 (12) C-1618 K Comparative | Sample Q 1531-121 (13) C-1218 K Comparative | Sample R 1531-122 (14) C-1214 K Comparative |
|---|---|---|---|---|
| Wt. Crystallizing Agent | 1.504 g | 1.515 g | 1.509 g | 1.511 g |
| (1) Water | 41.607 g | 43.533 g | 42.195 g | 41.708 g |
| (18) NaOH | 6.963 g | 5.020 g | 6.435 g | 6.843 g |
| % Crystallizing Agent | 3.00 wt % | 3.03 wt % | 3.00 wt % | 3.02 wt % |
| Firmness | NM1 | NM1 | NM1 | NM1 |
| AP Expression | NM5 | NM5 | NM5 | NM5 |
| Temperature | NM3 | NM3 | NM3 | NM3 |
| Po | 0.26 | 0.25 | 0.27 | 0.28 |
| Ps | [0.74] | [0.69] | [0.58] | [0.72] |
| (Chain length distribution for each crystallizing agent) | | | | |
| HC8 | — | — | — | — |
| HC10 | — | — | — | — |
| HC12 | 1.113 g | — | 0.875 g | 1.088 g |
| HC13 | — | — | — | — |
| HC14 | 0.391 g | — | 0.287 g | 0.378 g |
| HC15 | — | — | — | — |
| HC16 | — | 0.300 g | 0.121 g | 0.045 g |
| HC17 | — | — | — | — |
| HC18 | — | 0.076 g | 0.226 g | — |
| HC18:1 | — | 1.045 g | — | — |
| Other | — | 0.106 g | — | — |

TABLE 6

|  | Sample S FG4011-31 Inventive | Sample T FG4011-32 Inventive | Sample U FG4011-33 Inventive | Sample V FG4011-35 Comparative |
|---|---|---|---|---|
| (1) Water | 47.501 g | 47.501 g | 47.500 g | 47.501 g |
| (2) NaC10 | — | 0.500 g | 1.000 g | 2.000 g |
| (3) NaC12 | — | — | — | — |
| (4) NaC14 | 2.500 g | 2.000 g | 1.505 g | 0.501 g |
| (5) NaC16 | — | — | — | — |
| (6) NaC18 | — | — | — | — |
| (7) NaC18:1 | — | — | — | — |
| % Crystallizing Agent | 5.0 wt % | 5.0 wt % | 5.1 wt % | 5.0 wt % |
| Firmness | 16.2N | 13.7N | 11.7N | NM1 |
| AP Expression | 8,107 J m−3 | 8,753 J m−3 | 2,176 J m−3 | NM5 |
| Temperature | 48.6° C. | 44.5° C. | 40.0° C. | NM3 |
| Po | 1.00 | 0.80 | 0.60 | 0.20 |
| Ps | 1.00 | 0.80 | 0.60 | [0.8] |

Example 3

This include example demonstrates the effect of sodium chloride addition on the thermal stability and firmness of the rheological solid composition. Examples AA-AD (TABLE 7) show the effect of adding sodium chloride into the hot mixture of crystallizing agent and aqueous phase. Example AA is the control, without sodium chloride addition. Example AB and Example AC have increasing amounts of sodium chloride which results in increasing thermal stability temperature, but with a slight decrease in firmness. Surprisingly, Example AD curds the hot mixture. Not wishing to be bound by theory, but it is believed the sodium chloride is thought to 'salt out' the crystallizing agent so that it becomes soluble only at higher temperature; and also changes the crystallization of the crystallizing agent resulting in slightly softer compositions. However, when the sodium chloride level is too high, the solubility temperature exceeds the processing temperature and the mixtures curd. Once curding has occurred, it can no longer form the crystalline mesh. Examples AE-AG demonstrate a solution to this problem. In these examples, the crystalline mesh is formed first and then the sodium chloride is physically added to the top of the rheological solid composition. In this progression, the sodium chloride concentration increases the thermal stability temperature, while not changing the firmness. Not wishing to be bound by theory, it is believed that the crystalline mesh is formed as in the control Example AA, and that the added sodium chloride diffuses through the composition to change the solubility of the fibrous crystallizing agent, but not the nature of the fibers. Curding is no longer a problem, as the mixtures are crystallized first before the salt addition. This approach provides a more than 20-degree increase in the thermal stability temperature.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples AA-AD were prepared by adding Water (1), Sodium Myristate (NaM (4)) and sodium chloride (16) to the beaker. The beaker was placed on the heating-pad assembly. The overhead stirrer was placed in the beaker and set to rotate at 100 rpm. The heater was set at 80° C. The preparation was heated to 70° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. Firmness measurements were made with the FIRMNESS TEST METHOD, thermal stability measurement was made by the THERMAL STABILITY TEST METHOD and purity was determined from the BLEND TEST METHOD. Examples AE-AG were prepared by adding Water (1) and NaM (4) the beaker. The beaker was placed on the heating-pad assembly. The overhead stirrer was placed in the beaker and set to rotate at 100 rpm. The heater was set at 70° C. The preparation was heated to 70° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. The sodium chloride (16) was added to the top of the composition and allowed to diffuse through the composition for one week, before measurement. Firmness measurements were made with the FIRMNESS TEST METHOD, thermal stability measurement was made by the THERMAL STABILITY TEST METHOD and purity was determined from the BLEND TEST METHOD. One skilled in art recognizes that cooling compositions of crystallizing agent at different rates may result in modest differences in the firmness, aqueous phase expression and stability temperature properties; this is common in samples prepared at different absolute weights.

TABLE 7

|  | Sample AA 1531-9 Inventive | Sample AB 1531-10 Inventive | Sample AC 1531-11 Inventive | Sample AD 1531-12 Comparative |
|---|---|---|---|---|
| (1) Water | 48.531 g | 48.070 g | 47.028 g | 43.742 g |
| (4) NaM | 1.519 g | 1.512 g | 1.478 g | 1.358 g |
| % Crystallizing Agent | 3.03 wt % | 3.02 wt % | 2.95 wt % | 2.70 wt % |
| (16) NaCl | — | 0.508 g | 1.524 g | 5.087 g |
| Wt % NaCl | — | 1.0 wt % | 3.0 wt % | 10.1 wt % |

TABLE 7-continued

|  | Sample AA 1531-9 Inventive | Sample AB 1531-10 Inventive | Sample AC 1531-11 Inventive | Sample AD 1531-12 Comparative |
|---|---|---|---|---|
| Firmness | 6.51N | 3.77N | 3.15N | NM2 |
| Stability Temp | 54.0° C. | 61.6° C. | 64.7° C. | NM4 |
| Po | 1.00 | 1.00 | 1.00 | 1.00 |
| Ps | 1.00 | 1.00 | 1.00 | 1.00 |

TABLE 8

|  | Sample AE 1531-13 Inventive | Sample AF 1531-14 Inventive | Sample AG 1531-15 Inventive |
|---|---|---|---|
| Water | 48.0 g | 47 g | 43.6 g |
| NaM | 1.5 g | 1.5 g | 1.35 g |
| % Crystallizing Agent | 3.00 wt % | 3.00 wt % | 2.70 wt % |
| NaCl (post) | 0.5 g | 1.5 g | 5.0 g |
| Wt % NaCl | 1.0 wt % | 3.0 wt % | 10.1 wt % |
| Firmness | 8.47N | 9.31N | 9.53N |
| Stability Temp | 55.5° C. | 61.7° C. | 76.7° C. |
| Po | 1.00 | 1.00 | 1.00 |
| Ps | 1.00 | 1.00 | 1.00 |

TABLE 9

|  | Sample AH FG4007-1 Comparative |
|---|---|
| (1) Water | 71.500 g |
| (16) NaCl | 1.002 g |
| (17) HL | 4.506 g (22.5 mmol) |
| (15) NaOH | 22.500 g (563 mmol) |
| % Crystallizing Agent | 5.0 wt % |
| Firmness | 11.43N |
| AP Expression | 2,810 J m−3 |
| Stability Temp. | 35.5° C. |
| Po | 0.00 |
| Ps | [1.00] |

Example 4

This example illustrates the difference between inventive samples in this specification relative to bar soap compositions, exemplified by Example AH. The example fails to meet all three performance criteria. Specifically, the thermal stability temperature of the composition is too low to effectively survive reliably on the shelf life or in the supply chain. Not wishing to be bound by theory, it is believed the chain length of 12 is far too soluble owing to the short chain length (i.e. Sample J) such that—even with a 1 wt % addition of the sodium chloride, the C12 solubilizes below 40° C.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

A solution was prepared by adding water (1), sodium chloride (16) and lauric acid (17) to the beaker. The beaker was placed on the heated mixing device. The overhead stirrer was placed in the beaker and set to rotate at 100 rpm. The heater was set and the preparation was heated to 70° C. Sodium hydroxide (15) was then added to the solution to neutralize the fatty acid and the entire mixture was heated to 95° C. The solution was then placed in cooling jars (Flak-Tech, Max 60 Cup Translucent, Cat #501 222t) and set on the bench to cool at room temperature 25 (±3° C.) until solid. Firmness measurements were made with the FIRMNESS TEST METHOD, thermal stability measurement was made by the THERMAL STABILITY TEST METHOD, water expression was made by the AQUEOUS PHASE EXPRESSION TEST METHOD and purity was determined from the BLEND TEST METHOD.

Example 5

Response of the Compositions to Shear Stress During Use; As shown in FIG. 3

As measured by amount of composition dispensed from a stick composition prepared from 3 wt % crystallizing agent in water, with practical process conditions.

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 125 ml stainless steel beaker (Thermo Fischer Scientific, Waltham, MA).

Solutions were prepared by adding water 97% water and 3% crystallizing agent (with specific chain length) to the beaker. The beaker was placed on the heated mixing device. The overhead stirrer was placed in the beaker and set to rotate at 225 rpm. The heater was set, and the preparation was heated to precisely 70° C. The solution was then poured in a face stick container (Qosmedix, Ronkonkoma, NY, Round Twist-Up Deodorant Container and Cap, Black, cat. no. 30006; Albea, France, Skyline Face Stick) and allowed to cool overnight at room temperature.

The plastic 'lid' was removed from the stick, and the stick was weighed. The stick was gently swiped across a human panelist's arm five times, then weighed again. This was repeated with at least three different panelists, and the differences averaged. The reported value in FIG. 3 is the average weight loss in grams of all three trials. A smaller value means less residue on the skin. Note: there is a discontinuous jump in the residue at C18. Not wishing to be bound by theory, it is thought that C18 (and longer chain length crystallizing agents) have both insufficient hydrophilic-hydrophobic balance and are too close (or above) practical process temperature, to form effective crystals and a crystalline mesh of fiber-like crystalline particles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rheological solid composition comprising:
a crystallizing agent; an aqueous phase comprising at least about 80 wt % water; and NaCl;
wherein, the rheological solid composition has a firmness between about 1.0 N to about 20.0 N as determined by the FIRMNESS TEST METHOD using a texture analyzer at room temperature;
a thermal stability of about 40° C. to about 95° C. as determined by the THERMAL STABILITY TEST METHOD using a differential scanning calorimeter (DSC);
a liquid expression of between about 100 J m-3 to about 8,000 J m-3 as determined by the AQUEOUS PHASE EXPRESSION TEST METHOD using a rheometer at room temperature; and
wherein the crystallizing agent is a blend of sodium salts of fatty acids containing from 13 to 17 carbon atoms; wherein the crystallizing agent blend has an Optimal Purity (Po) of greater than about 0.3 and a Single Purity (Ps) of greater than about 0.5 as determined by the BLEND TEST METHOD;
wherein the amount of crystallizing agent in the composition is between about 0.5% and 7.0% by weight of the rheological solid composition.

2. The composition of claim 1, wherein the rheological solid composition comprises a NaCl concentration of at most 10 wt %.

3. The composition of claim 1, wherein the Optimal Purity (Po) is greater than about 0.5.

4. The composition of claim 1, wherein the Optimal Purity (Po) is greater than about 0.7.

5. The composition of claim 1, wherein the Optimal Purity (Po) is greater than about 0.8.

6. The composition of claim 1, wherein the Single Purity (Ps) is greater than about 0.6.

7. The composition of claim 1, wherein the Single Purity (Ps) is greater than about 0.7.

8. The composition of claim 1, wherein the Single Purity (Ps) is greater than about 0.9.

9. The rheological solid composition of claim 1 wherein the sodium salts are at least two of sodium palmitate, sodium myristate, sodium tridecanoate, sodium pentadecanoate, and sodium heptadecanoate.

10. The rheological solid composition of claim 1 wherein the crystallizing agent is present in an amount from about 1% to about 5% by weight of the rheological solid composition.

11. The rheological solid composition of claim 1 wherein the crystallizing agent is present in an amount from about 2% to about 4% by weight of the rheological solid composition.

12. The rheological solid composition of claim 1, wherein, the rheological solid composition has the firmness between about 5.0 N to about 10.0 N as determined by the FIRMNESS TEST METHOD using the texture analyzer at room temperature.

13. The rheological solid composition of claim 1, wherein the rheological solid composition has the thermal stability from about 45° C. to about 80° C. as determined by the THERMAL STABILITY TEST METHOD using the DSC.

14. The rheological solid composition of claim 1, wherein the rheological solid composition has the thermal stability from about 50° C. to about 95° C. as determined by the THERMAL STABILITY TEST METHOD using a TA Q Series using the DSC.

15. The rheological solid composition of claim 1, wherein the rheological solid composition has the liquid expression of between about 1,000 J m-3 to about 7,000 J m-3 as determined by the AQUEOUS PHASE EXPRESSION TEST METHOD using the rheometer at room temperature.

16. The rheological solid composition of claim 1, wherein the rheological solid composition has the liquid expression of between about 2,000 J m-3 to about 5,000 J m-3 as determined by the AQUEOUS PHASE EXPRESSION TEST METHOD using the rheometer at room temperature.

\* \* \* \* \*